United States Patent
Hein et al.

(10) Patent No.: US 7,623,691 B2
(45) Date of Patent: Nov. 24, 2009

(54) METHOD FOR HELICAL WINDMILL ARTIFACT REDUCTION WITH NOISE RESTORATION FOR HELICAL MULTISLICE CT

(75) Inventors: Ilmar A. Hein, Schaumburg, IL (US); Katsuyuki Taguchi, Buffalo Grove, IL (US); Michael D. Silver, Northbrook, IL (US)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 704 days.

(21) Appl. No.: 10/912,183

(22) Filed: Aug. 6, 2004

(65) Prior Publication Data
US 2006/0029285 A1 Feb. 9, 2006

(51) Int. Cl.
*G06K 9/00* (2006.01)
(52) U.S. Cl. .................. 382/128; 382/131; 378/4; 378/21; 600/407
(58) Field of Classification Search .......... 382/128, 382/131, 132
See application file for complete search history.

(56) References Cited

U.S. PATENT DOCUMENTS

| | | | | | |
|---|---|---|---|---|---|
| 5,301,108 | A | * | 4/1994 | Hsieh | 378/8 |
| 5,377,250 | A | * | 12/1994 | Hu | 378/15 |
| 5,473,655 | A | * | 12/1995 | Hu | 378/4 |
| 5,561,695 | A | * | 10/1996 | Hu | 378/8 |
| 5,602,934 | A | * | 2/1997 | Li et al. | 382/128 |
| 5,845,003 | A | * | 12/1998 | Hu et al. | 382/131 |
| 6,466,700 | B1 | * | 10/2002 | Makram-Ebeid | 382/265 |
| 6,778,692 | B1 | * | 8/2004 | Yazici | 382/132 |
| 6,813,374 | B1 | * | 11/2004 | Karimi et al. | 382/131 |
| 6,885,764 | B2 | * | 4/2005 | Wang et al. | 382/131 |

OTHER PUBLICATIONS

Heucsher-D-J, Reduced partial volume artifacts using spiral CT and integrating interpolator, Feb.1999,Datastar,Medical physics vol. 26 pp. 276-286 (Abstract only) # 0006165752.*

(Continued)

*Primary Examiner*—Brian P Werner
*Assistant Examiner*—Jayesh Patel
(74) *Attorney, Agent, or Firm*—Oblon, Spivak, McClelland, Maier & Neustadt, L.L.P.

(57) ABSTRACT

A method of removing an imaging artifact in a medical image, including obtaining a first plurality of images, the first plurality of images collectively defining a first image volume; filtering the first plurality of images to create a second plurality of images, each image in the second plurality of images comprising an average of at least two images in the first plurality of images; selecting a first image from the first plurality of images; adding a lost noise image to a second image in the second plurality of images to create a noise restored image, the second image in the second plurality of images corresponding to the first image in the first plurality of images; determining a gradient image based on pixel values in the second plurality of images, the gradient image comprising a gradient value at each pixel location in the second image; and combining, based on the determined gradient image, the first image and the noise restored image to obtain a corrected image that does not contain the imaging artifact.

34 Claims, 7 Drawing Sheets

OTHER PUBLICATIONS

Zonneveld_F-W, The relationship between slice thickness and Image quality in CT, 1984, Medicamundi, pp. 104-117 (abstract only), # 0002552990.*

Silver-M, Windmill artfact in Multi slice helical CT, 2003, Medical imaging, pp. 1918-1927 (abstract only), # 0008033671.*

Heuscher-D-J, Reduced partial volume artifacts using spiral CT and integrating interpolator, Feb. 1999, Datastar, Medical physics vol. 26 pp. 276-286 (Abstract only) # 0006165752.*

Zonneveld F.W, The relationship between slice thickness and image quality in CT, 1984, Mediacmundi, pp. 104-117 (Abstract only), # 0002552990.*

Silver-M, Windmill artifacts in multi slice CT, 2003, Medical imaging, pp. 1918-1927 (Abstract only), # 0008033671.*

* cited by examiner

METHOD FOR HELICAL WINDMILL ARTIFACT REDUCTION WITH NOISE RESTORATION FOR HELICAL MULTISLICE CT

BACKGROUND OF THE INVENTION

1. Field of the Invention

The present invention relates generally to the enhancement and filtering of medical images to remove artifacts. The present invention also generally relates to computerized techniques for automated analysis of medical images, for example, as disclosed in U.S. Pat. No. 5,825,842, which is incorporated herein by reference.

2. Discussion of the Background

In X-ray CT imaging, it is common to low-pass filter or average a number of higher resolution images ("thin" images) in order to reduce artifacts or for other reasons. Typically, the filtering or averaging is performed in the axial direction, which is the direction perpendicular to the plane of the images (i.e., the z direction). The low-pass filtering is referred to as slice thickening because the effective "thickness" of the resulting image slice is larger. The undesirable effect of slice thickening is that image resolution is lost. This includes both resolution of the object of interest (OOI) being imaged, as well as background noise resolution. The effect of reduced noise resolution is that the grain size of the background noise pattern in the z direction is stretched. This is undesirable from a clinical standpoint, especially when viewing images in a coronal or sagittal format.

Images produced from helical multi-slice CT systems exhibit a distinct type of artifact when operated at medium and high helical pitch values. The artifacts appear as alternating light and dark regions around structures whose features change axially. The shape of the artifact is similar to the vanes on a windmill; hence the name "windmill" artifact. This artifact has also been referred to as simply the "helical" artifact in the literature. A common case is a higher density bone structure surrounded by lower density soft tissue. The windmill artifact appears as light and dark alternating "vanes" in the soft tissue emanating from the bone structure. The cause of the artifact is inadequate sampling in the axial direction due to the high helical pitch. This is purely a function of geometry and will occur with all helical multi-slice CT reconstruction algorithms. Images with windmill artifacts are referred to as "artifact" images. Most methods of reducing the windmill artifact also result in smoothing of sharp edges and other structures as well as noise. Such images are referred to as "smooth" images.

SUMMARY OF THE INVENTION

Accordingly, in order to overcome the problems described above, the present invention is directed to a system, method, and computer program product that corrects the windmill artifact and retains the sharpness of edges and background noise patterns.

Accordingly, there is provided a method, system, and computer program product for removing an artifact in a medical image, comprising: (1) obtaining a first plurality of images, the first plurality of images collectively defining a first image volume; (2) filtering the first plurality of images to create a second plurality of images, each image in the second plurality of images comprising an average of at least two images in the first plurality of images; selecting a first image from the first plurality of images; (3) adding a lost noise image to a second image in the second plurality of images to create a noise restored image, the second image in the second plurality of images corresponding to the first image in the first plurality of images; (4) determining a gradient image based on pixel values in the second plurality of images, the gradient image comprising a gradient value at each pixel location in the second image; and (5) combining, based on the determined gradient image, the first image and the noise restored image to obtain a corrected image that does not contain the imaging artifact.

Further, according to an embodiment of the present invention, the above method further comprises: (1) obtaining pure noise images corresponding to the first plurality of images; (2) filtering the pure noise images to create respective thick noise images, each thick noise image being a weighted average of at least two of the pure noise images; and (3) subtracting a thick noise image corresponding to the first image from a corresponding pure noise image to create the lost noise image.

According to an aspect of the present invention, the determining step comprises: (1) calculating, at each location in the second image, directional gradient values that are each based on an absolute value of a change in image intensity at two pixel locations having coordinates that differ only in a respective direction; and (2) determining the gradient value at each pixel location in the second image as a weighted average of the directional gradient values.

According to another aspect of the present invention there is provided an X-ray computed tomography (CT) system, comprising: (1) an X-ray generator configured to generate a cone-bean X-ray that passes through an object; (2) an X-ray detector configured to output projection data based on said X-ray passing through said object; (3) a reconstruction processing device configured to generate a CT volume image based on said projection data output by said X-ray detector, the CT volume image comprising a plurality of two-dimensional images; (4) a gradient calculation unit configured to calculate at least one gradient value of said generated CT volume image in an axial direction; and (5) an image filtering unit configured to filter said CT volume image, based on the at least one calculated gradient value, to generate a filtered CT volume image in which an appearance of an imaging artifact is reduced.

According to another aspect of the present invention, there is provided a method of processing a medical image, comprising: (1) obtaining a first plurality of images, the first plurality of images collectively defining a first image volume; (2) filtering the first plurality of images to create a second plurality of images, each image in the second plurality of images comprising an average of at least two images in the first plurality of images; (3) selecting a first image from the first plurality of images; (4) determining a gradient image based on pixel values in the second plurality of images, the gradient image comprising a gradient value at each pixel location in the second image; and (5) combining, based on the determined gradient image, the first image and a second image in the second plurality of images to obtain a corrected image in which an appearance of an imaging artifact is reduced, the second image in the second plurality of images corresponding to the first image in the first plurality of images.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, in which like reference numerals refer to identical or corresponding parts throughout the several views, and in which.

DETAILED DESCRIPTION OF THE PREFERRED EMBODIMENTS

Figure 1:
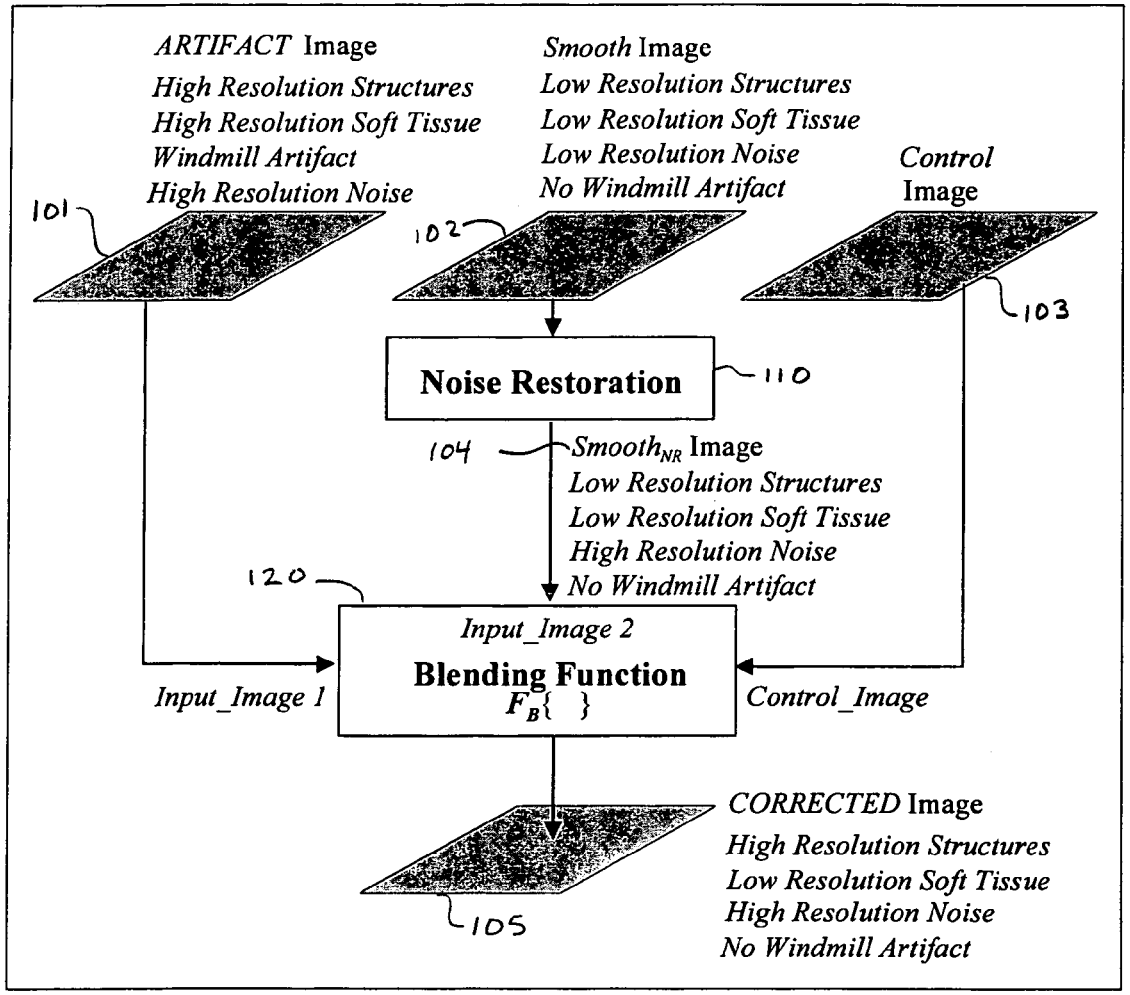
FIG. 1 illustrates a system for windmill artifact reduction with noise restoration according to an embodiment of the present invention.

The present invention is directed to a system, method, and computer program product that corrects the windmill artifact and retains the sharpness of edges and background noise patterns. As shown in FIG. 1, an artifact image 101 and a smooth image 104 are combined to form a corrected image 105. This is accomplished by an adaptive blending of two input images, i.e., artifact image 101 and smooth image 104, where a control image 103 and blending function 120 ($F_B\{\}$) determine how the input images are blended. Further, smooth image 104 is the output of Noise Restoration Unit 110, which restores high resolution noise to smooth image 102, as shown in FIG. 1.

Figure 2:
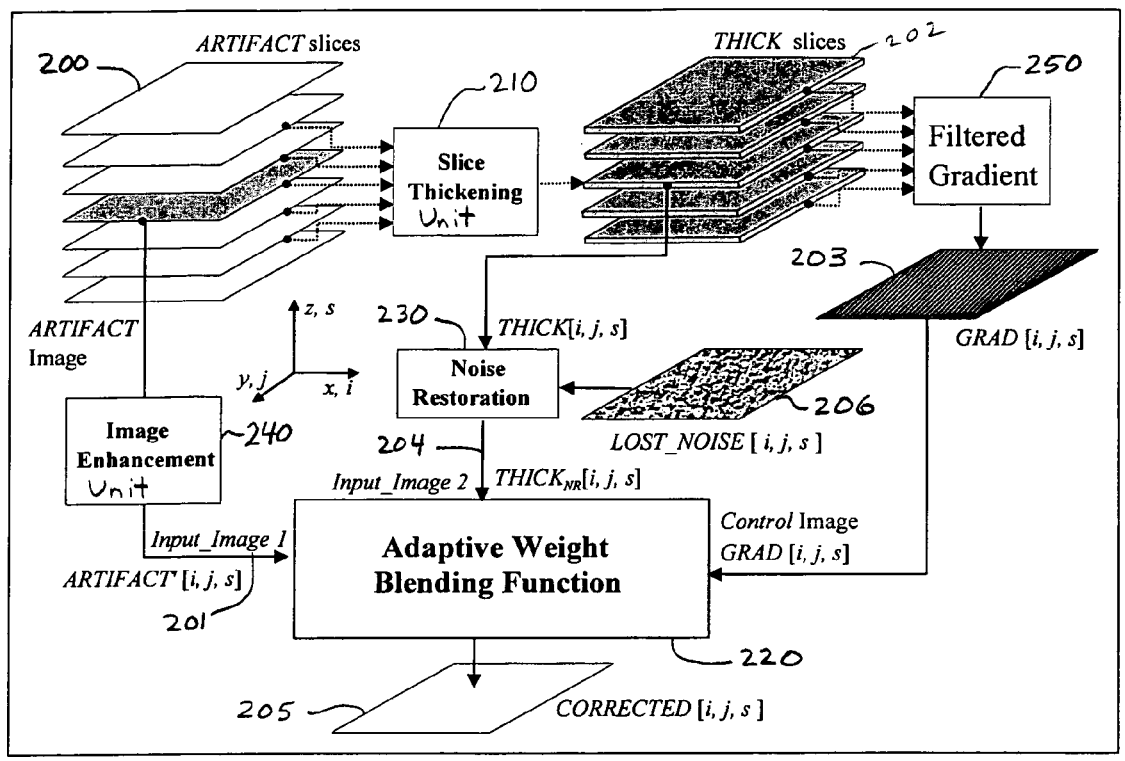
FIG. 2 illustrates a system diagram of the preferred embodiment of the present invention.

A system corresponding to the preferred embodiment of the present invention is shown in FIG. 2. Generally, the i and j indexes represent pixels in the lateral x and y directions, and the s index represents the slice position in the axial z direction. The input is the artifact image volume 200, which comprises a plurality of artifact image slices that are obtained, e.g., by a CT imaging apparatus.

The control image 203 and the smooth image 204 are created from an image in the artifact image volume 200, although, in other embodiments, the control image 203 may be based on other sources or criterion different from the artifact image volume 200. Alternatively, other processing of the artifact image volume 200 may be implemented instead of smoothing, such as sharpening. The image slices from the artifact image volume 200 are smoothed by "thickening" the artifact slice by a slice thickening unit 210, which is described in more detail below. In other embodiments, slice thickening can be a different function than thickening, such as slice thinning, or some other function. The resulting thick image volume 202 has reduced windmill artifacts along with reduced structure and reduced noise resolution. The noise resolution in an image in the thick image volume 202 is restored by the noise restoration unit 230 by adding lost noise 206, which is similar to that lost by the slice thickening unit 210. The resulting thick$_{NR}$ image 204 is input (input image 2) to the Adaptive Weight Blending Function 220, which produces the corrected image 205. The control image 203 is created by the filtered gradient unit 250, which processes the thick image volume 202. In other embodiments, the control image 203 can be created from the thick image volume 202 using a function different than the gradient function. In one embodiment, an artifact image from the artifact image volume 200 is enhanced by the Image Enhancement Unit 240 to further sharpen edges prior to blending. The enhanced image still contains windmill artifacts, and is referred to as artifact image 201 to indicate that it is an enhanced version of the artifact image. The artifact image 201 is input (input image 1) to the Adaptive Weight Blending Function 220, as shown in FIG. 2.

Slice Thickening

The Slice Thickening Unit 210 averages a number of artifact slices from the artifact image volume 200. The average can be a non-weighted average, a weighted average, an adaptively determined weighted average, or other method of combining artifact slices that results in a reduced windmill artifact and reduced image and noise resolution. In the preferred embodiment, a weighted average low-pass filter is implemented to produce images in the thick image volume 202 as follows:

$$THICK[i, j, s] = \sum_{c=-N_{TAvg}/2}^{N_{TAvg}/2} W_{Thk}[c] \cdot ARTIFACT[i, j, s+c] \quad (1)$$

where $N_{TAvg}$ is the number of slices used in averaging and $W_{Thk}[c]$ are the weights. In other embodiments, a different method of slice thickening can be employed.

Noise Restoration

Figure 3:
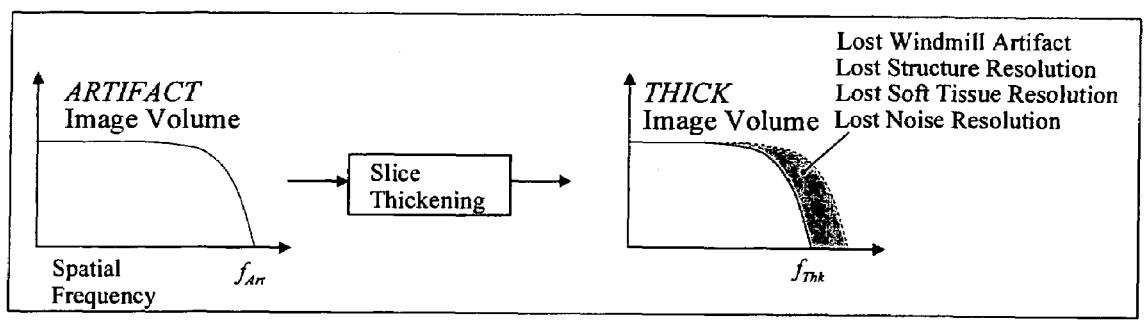
FIG. 3 illustrates the low-pass filtering effect of slice thickening.
Figure 4:
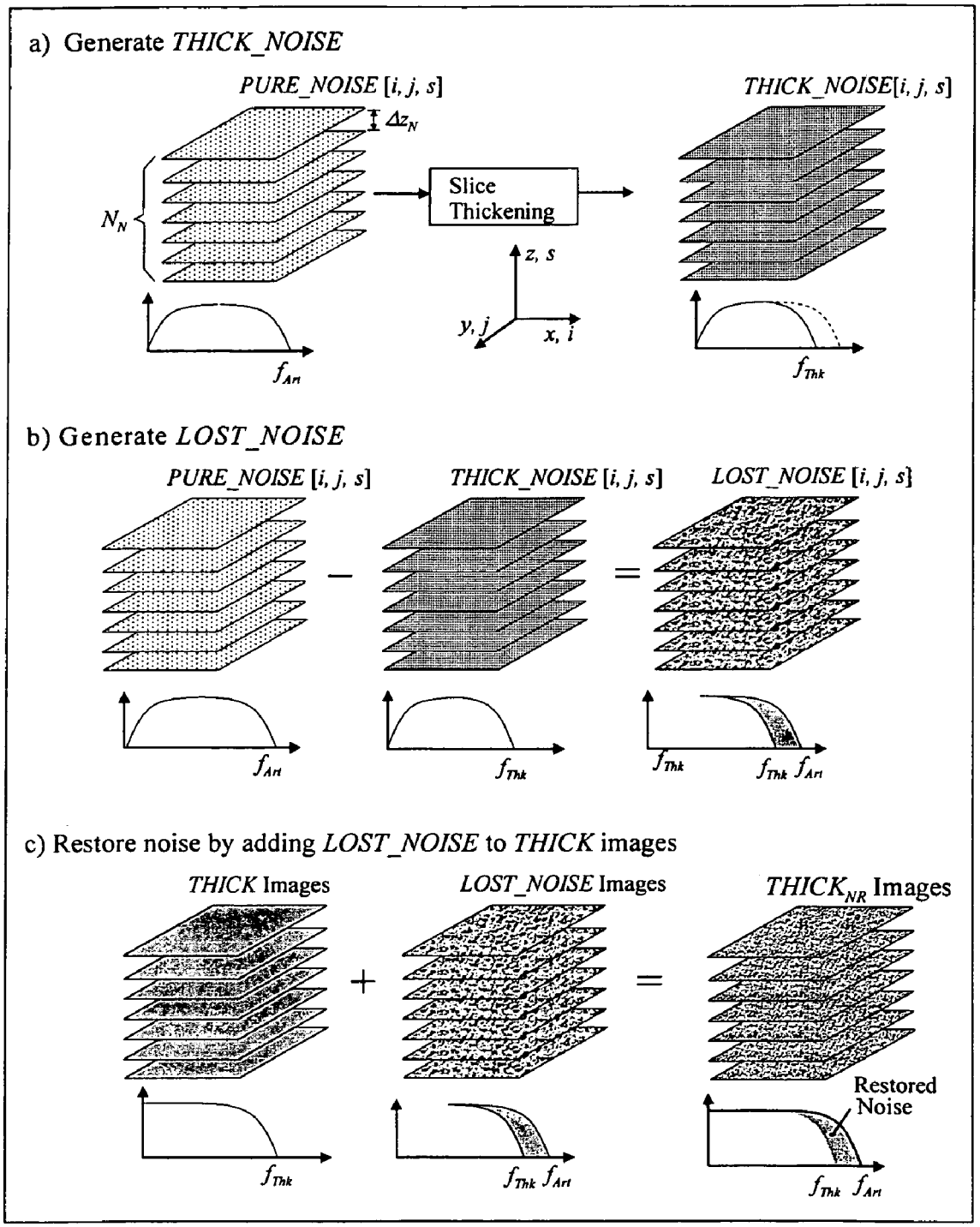
FIGS. 4a, 4b, and 4c are illustrations of the restoration of lost noise according to an embodiment of the present invention.

The low-pass filtering of the slice thickening step removes high frequency spatial components, as shown in the shaded region in FIG. 3. The removed frequencies are those that contribute to the windmill artifact, as well as those representing tissue structures and noise. One consequence of the reduced noise resolution is that the grain size of the background noise pattern in the z direction is stretched. This is undesirable from a clinical standpoint when viewing images in a coronal or sagittal format. The noise restoration unit 230 restores the background noise pattern to that of the artifact images by adding back a lost noise image 206 to images in the thick image volume, as shown in FIGS. 4a-4c. The noise restoration unit 230 performs the following four steps:

(1) Generate or Acquire Noise Image Volume

A pure noise image volume with noise characteristics the same as the artifact image must be generated or acquired. The number of images $N_N$ and slice spacing $\Delta z_N$ of the artifact image volume must be sufficient to adequately sample the noise pattern in the z direction. The noise pattern is a function of system parameters kV, mA, helical pitch, slice spacing, detector segment width; and reconstruction parameters FOV, slice spacing, convolution kernel, and image thickness. The pure noise volume can be generated mathematically or acquired physically. In the preferred embodiment, pure noise images are acquired from a water phantom for a limited number of acquisition and reconstruction parameter settings, and interpolated to match the true acquisition and reconstruction setting for the artifact image volume 200.

(2) Thicken the Pure Noise Volume

As shown in FIG. 4a, the pure noise volume is thickened using the same parameters and the same procedure used for the thick image volume 202. See FIG. 3.

(3) Subtract Thick Noise Image Volume from Pure Noise Image Volume to Create a Lost Noise Volume As shown in FIG. 4b, the thick noise images are subtracted from corresponding pure noise images. The result is an image volume containing only the lost noise frequencies:

$$\text{LOST\_NOISE}[i, j, s] = \text{PURE\_NOISE}[i, j, s] - \text{THICK\_NOISE}[i, j, s] \qquad (2)$$

(4) Add the Lost Noise Images to the Thick Images

As shown in FIG. 4c, the lost noise images are added to corresponding thick images as follows:

$$\text{THICK}_{NR}[i, j, s] = \text{LOST\_NOISE}[i, j, s] + \text{THICK}[i, j, s] \qquad (3)$$

where $\text{thick}_{NR}$ is the noise-restored thick image. In an alternative embodiment, noise restoration can be implemented after blending, with the lost noise added to the corrected image 205.

Filtered Gradient Image Calculation

The filtered gradient image can be created from the x, y, and z gradients of either the artifact or thick image data. In the preferred embodiment, the thick image data is used, and the gradients are calculated from the absolute value of the change in intensity at two pixel locations in the gradient direction (x, y, or z):

$$xGrad[i, j, s] = \frac{|THICK(i_2, j, s) - THICK(i_1, j, s)|}{i_2 - i_1} \qquad (4)$$

$$yGrad[i, j, s] = \frac{|THICK(i, j_2, s) - THICK(i, j_1, s)|}{j_2 - j_1} \qquad (5)$$

$$zGrad[i, j, s] = \frac{|THICK(i, j, s_2) - THICK(i, j, s_1)|}{s_2 - s_1} \qquad (6)$$

In other embodiments, a non-absolute value gradient can be calculated.

To reduce the effects of noise, each gradient is low-pass filtered along its gradient direction. In the preferred embodiment, the low-pass filtering is implemented with a weighted-average filter as follows:

$$xGradFilt[i, j, s] = \sum_{c=-N_{xGF}/2}^{N_{xGF}/2} W_{xGF}[c] \cdot xGrad[i+c, j, s] \qquad (7)$$

$$yGradFilt[i, j, s] = \sum_{c=-N_{yGF}/2}^{N_{yGF}/2} W_{yGF}[c] \cdot yGrad[i, j+c, s] \qquad (8)$$

$$zGradFilt[i, j, s] = \sum_{c=-N_{zGF}/2}^{N_{zGF}/2} W_{zGF}[c] \cdot zGrad[i, j, s+c] \qquad (9)$$

where $W_{xGF}[c]$, $W_{yGF}[c]$, and $W_{zGF}[c]$, are the averaging weights. In other embodiments, no filtering, a different type of filtering, or adaptive filtering can be implemented.

The final gradient image is created by combining the individual filtered gradient images. In the preferred embodiment, a weighted average is used:

$$\text{Grad}[i, j, s] = W_x \cdot xGradFilt[i, j, s] + W_y \cdot yGradFilt[i, j, s] + W_z \cdot zGradFilt[i, j, s] \qquad (10)$$

where $W_x$, $W_y$, and $W_z$ are the weights for each directional gradient.

Adaptive Weight Blending Function

Figure 5:
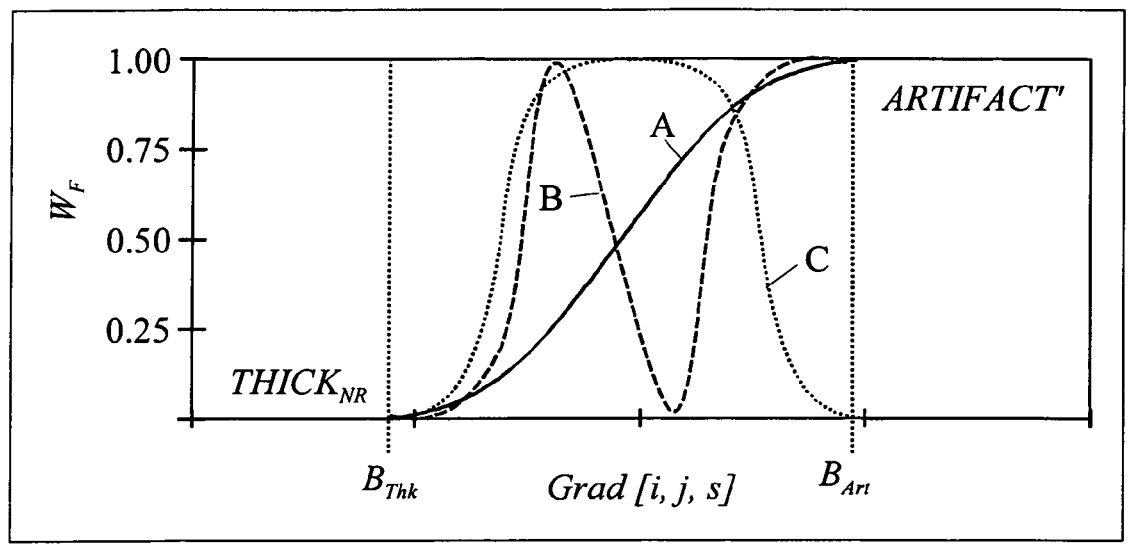
FIG. 5 is an illustration of adaptive weight functions, showing curves A (smooth transition), B and C (selective transitions)

As shown in FIG. 5, the adaptive weight blending function 220 is based on an adaptive weight curve $W_F$, that exhibits a smooth transition from the $\text{thick}_{NR}$ to artifact' image. Three examples are shown in FIG. 5. Curve A in FIG. 5 allows for a direct smooth transition from the $\text{thick}_{NR}$ to artifact image. Curves B and C allow for a selective transition, in which structure with particular gradients in the artifact' image can be suppressed. Curve A is implemented in the preferred embodiment. Depending on the particular application, different transition curves can be incorporated in different embodiments. The break values $B_{Thk}$ and $B_{Art}$ determine the range of adaptive weighting. Thus, the corrected image 205 is determined using the formula:

$$\text{CORRECTED}[i, j, s] = W_f\{GRAD[i, j, s]\} \cdot \text{ARTIFACT}[i, j, s] + (1 - W_f\{GRAD[i, j, s]\}) \cdot \text{THICK}_{NR}[i, j, s] \qquad (11)$$

In the preferred embodiment, $W_F$ is given by curve A in FIG. 5. In particular, $W_F$ is calculated as follows:

$$W_f\{GRAD\} = 0.0 \text{ if } 0 \leq GRAD < B_{Thk} \qquad (12)$$

$$2 \cdot \left[\frac{GRAD - B_{Thk}}{B_{Art} - B_{Thk}}\right]^2 \text{ if } B_{Thk} \leq GRAD < B_o \qquad (13)$$

$$0.5 + 2 \cdot \left[\frac{GRAD - B_o}{B_{Art} - B_{Thk}}\right] - 2 \cdot \left[\frac{z\_GRAD - B_o}{B_{Art} - B_{Thk}}\right]^2 \text{ if } \qquad (14)$$

$$B_o \leq GRAD \leq B_{Art}$$

$$1.0 \text{ if } GRAD > B_{Art} \qquad (15)$$

where $$B_o = \frac{B_{Thk} + B_{Art}}{2}$$

Image Enhancement

Depending on the application, enhancement of the artifact image by the image enhancement unit 240 may be required. In different embodiments, image enhancement can be a sharpening of the artifact image in order to enhance edges, thickening of the artifact image, or some other image processing function, as well as no enhancement of the artifact image.

Figure 6:
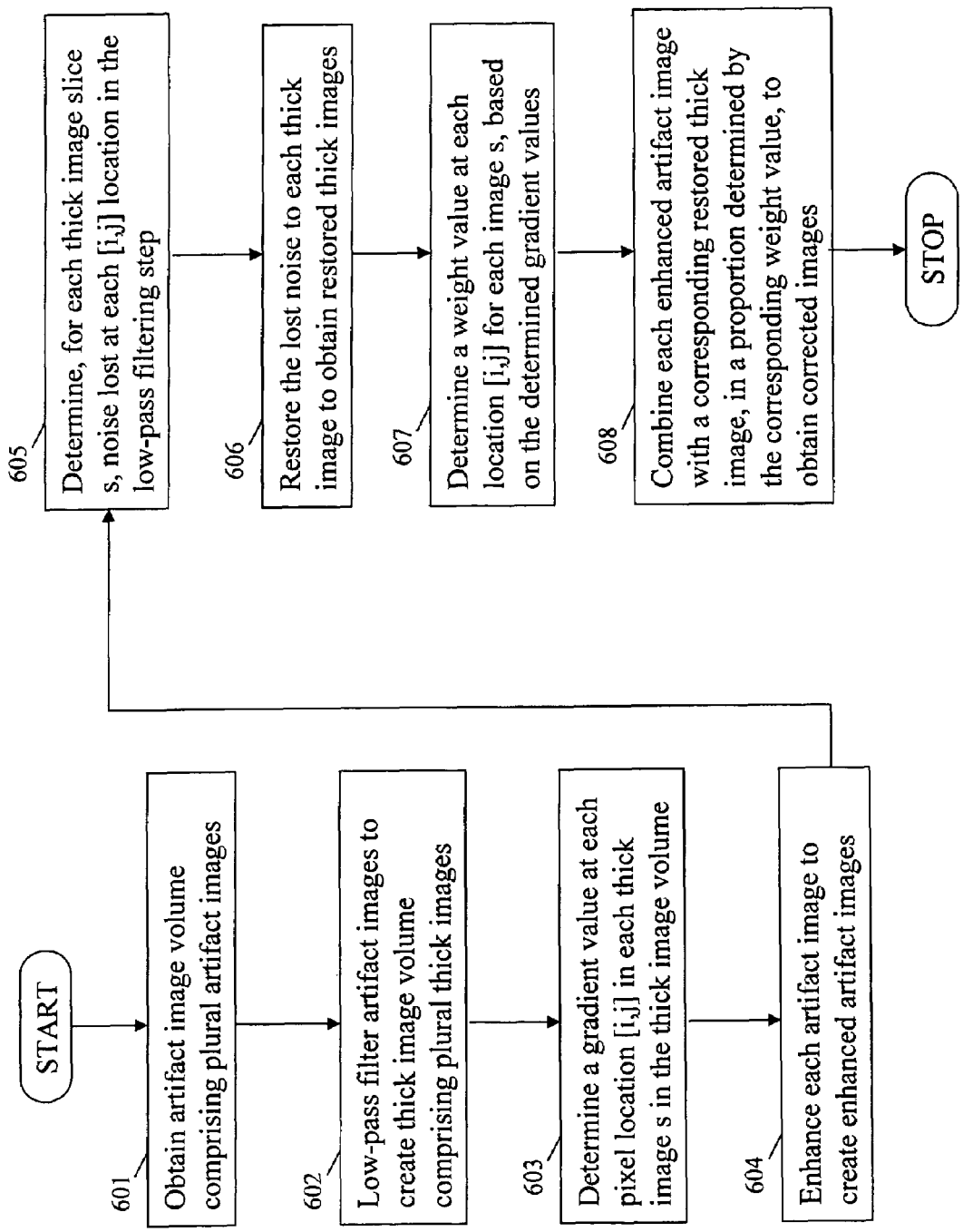
FIG. 6 is an illustration of the steps in a method of artifact reduction according to an embodiment of the present invention.

FIG. 6 illustrates the steps in a method for removing artifacts in a medical image according to an embodiment of the present invention.

In step 601, artifact images representing an artifact image volume are obtained, e.g., by using a computed tomography imaging system. Each artifact image slice s has a number of image pixels in the x and y directions, which are indexed by indices i and j, respectively. Accordingly, a voxel in the artifact image volume can be represented by the indices s, i, and j.

In step 602, each artifact image is filtered to create a thick image volume comprising plural thick images, e.g., using Equation (1) above.

In step 603, a gradient value in each direction is determined at each voxel location, i.e., at each pixel location [i,j] within each image slice within the thick image volume. As discussed above, Equations (4)-(10) can be used to determine a weighted/filtered gradient value at each location [i,j] in each slice s. The resulting gradient values for an image slice s can be thought of as a gradient "image."

In step 604, each artifact image is enhanced to create enhanced artifact images. As described above, image enhancement can be a sharpening of each artifact image in order to enhance edges, thickening of the artifact image, or some other image processing function.

In step 605, the amount of noise lost in the filtering step 602 is determined for each thick slice, as described above with reference to FIGS. 4a and 4b and Equation (2).

In step 606, the lost noise is added back to the thick image slices comprising the thick image volume to create restored thick images, as described above with reference to FIG. 4c and Equation (3).

In step 607, a weight value is determined at each [i,j] location for each image s based on the gradient values determined in step 603. For example, Equations (12)-(15) can be used to compute the curve A shown in FIG. 5, which is a function relating a gradient value at location [i,j] in an image slice s to a weight value $W_F$, which is used to combine the enhanced images and the restored thick images in step 608.

In step 608, each artifact image is combined with a corresponding restored thick image, using the weight values $W_F$, to obtain a corresponding corrected image according to Equation (11).

Figure 7:
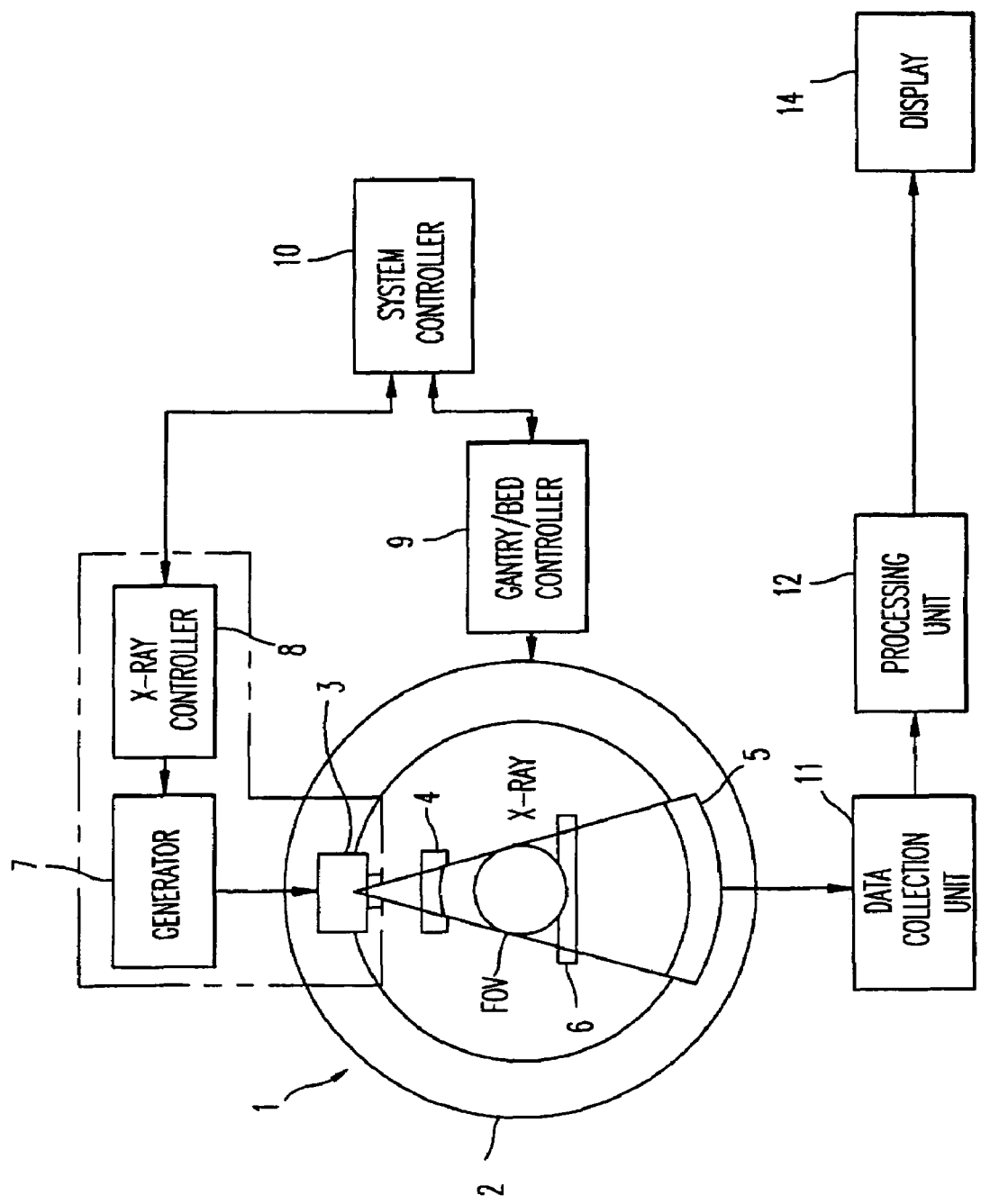
FIG. 7 is an illustration of an X-ray computed tomographic (CT) imaging device.

FIG. 7 shows an x-ray computed topographic imaging device that can be used to obtain images processed by methods of the present invention. The projection data measurement system constituted by gantry 1 accommodates an x-ray source 3 that generates a cone-beam of x-ray flux approximately cone-shaped, and a two-dimensional array type x-ray detector 5 consisting of a plurality of detector elements arranged in two-dimensional fashion, i.e., a plurality of elements arranged in one dimension stacked in a plurality of rows. X-ray source 3 and two-dimensional array type x-ray detector 5 are installed on a rotating ring 2 in facing opposite sides of a subject, who is laid on a sliding sheet of a bed 6. Two-dimensional array type x-ray detector 5 is mounted on rotating ring 2. Each detector element will correspond with one channel. X-rays from x-ray source 3 are directed on to subject through an x-ray filter 4. X-rays that have passed through the subject are detected as an electrical signal by two-dimensional array type x-ray detector 5.

X-ray controller 8 supplies a trigger signal to high voltage generator 7. High voltage generator 7 applies high voltage to x-ray source 3 with the timing with which the trigger signal is received. This causes x-rays to be emitted from x-ray source 3. Gantry/bed controller 9 synchronously controls the revolution of rotating ring 2 of gantry 1 and the sliding of the sliding sheet of bed 6. System controller 10 constitutes the control center of the entire system and controls x-ray controller 8 and gantry/bed controller 9 such that, as seen from the subject, x-ray source 3 executes so-called helical scanning, in which it moves along a helical path. Specifically, rotating ring 2 is continuously rotated with fixed angular speed while the sliding plate is displaced with fixed speed, and x-rays are emitted continuously or intermittently at fixed angular intervals from x-ray source 3.

The output signal of two-dimensional array type x-ray detector 5 is amplified by a data collection unit 11 for each channel and converted to a digital signal, to produce projection data. The projection data that is output from data collection unit 11 is fed to reconstruction processing unit 12. Reconstruction processing unit 12 uses the projection data to find backprojection data reflecting the x-ray absorption in each voxel. In the helical scanning system using a cone-beam of x-rays as in the first embodiment, the imaging region (effective field of view) is of cylindrical shape of radius ω centered on the axis of revolution. Reconstruction processing unit 12 defines a plurality of voxels (three-dimensional pixels) in this imaging region, and finds the backprojection data for each voxel. The three-dimensional image data or tomographic image data compiled by using this backprojection data is sent to display device 14, where it is displayed visually as a three-dimensional image or tomographic image.

For the purposes of this description we shall define an image to be a representation of a physical scene, in which the image has been generated by some imaging technology. Examples of imaging technology could include television or CCD cameras or X-ray, sonar or ultrasound imaging devices. The initial medium on which an image is recorded could be an electronic solid-state device, a photographic film, or some other device such as a photostimulable phosphor. That recorded image could then be converted into digital form by a combination of electronic (as in the case of a CCD signal) or mechanical/optical means (as in the case of digitizing a photographic film or digitizing the data from a photostimulable phosphor).

All embodiments of the present invention conveniently may be implemented using a conventional general purpose computer or micro-processor programmed according to the teachings of the present invention, as will be apparent to those skilled in the computer art. Appropriate software may readily be prepared by programmers of ordinary skill based on the teachings of the present disclosure, as will be apparent to those skilled in the software art. In particular, the computer housing may house a motherboard that contains a CPU, memory (e.g., DRAM, ROM, EPROM, EEPROM, SRAM, SDRAM, and Flash RAM), and other optional special purpose logic devices (e.g., ASICS) or configurable logic devices (e.g., GAL and reprogrammable FPGA). The computer also includes plural input devices, (e.g., keyboard and mouse), and a display card for controlling a monitor. Additionally, the computer may include a floppy disk drive; other removable media devices (e.g. compact disc, tape, and removable magneto-optical media); and a hard disk or other fixed high density media drives, connected using an appropriate device bus (e.g., a SCSI bus, an Enhanced IDE bus, or an Ultra DMA bus). The computer may also include a compact disc reader, a compact disc reader/writer unit, or a compact disc jukebox, which may be connected to the same device bus or to another device bus.

Examples of computer readable media associated with the present invention include compact discs, hard disks, floppy disks, tape, magneto-optical disks, PROMs (e.g., EPROM, EEPROM, Flash EPROM), DRAM, SRAM, SDRAM, etc. Stored on any one or on a combination of these computer readable media, the present invention includes software for controlling both the hardware of the computer and for enabling the computer to interact with a human user. Such software may include, but is not limited to, device drivers, operating systems and user applications, such as development tools. Computer program products of the present invention include any computer readable medium which stores computer program instructions (e.g., computer code devices) which when executed by a computer causes the computer to perform the method of the present invention. The computer code devices of the present invention may be any interpretable or executable code mechanism, including but not limited to, scripts, interpreters, dynamic link libraries, Java classes, and complete executable programs. Moreover, parts of the processing of the present invention may be distributed (e.g., between (1) multiple CPUs or (2) at least one CPU and at least one configurable logic device) for better performance, reliability, and/or cost. For example, an outline or image may be selected on a first computer and sent to a second computer for remote diagnosis.

The invention may also be implemented by the preparation of application specific integrated circuits or by interconnecting an appropriate network of conventional component circuits, as will be readily apparent to those skilled in the art.

The source of image data to the present invention may be any appropriate image acquisition device such as an X-ray machine, CT apparatus, and MRI apparatus. Further, the acquired data may be digitized if not already in digital form. Alternatively, the source of image data being obtained and processed may be a memory storing data produced by an image acquisition device, and the memory may be local or remote, in which case a data communication network, such as PACS (Picture Archiving Computer System), may be used to access the image data for processing according to the present invention.

Of course, the particular hardware or software implementation of the present invention may be varied while still remaining within the scope of the present invention. It is therefore to be understood that within the scope of the appended claims and their equivalents, the invention may be practiced otherwise than as specifically described herein.

The invention claimed is:

1. A method of processing a medical image, comprising:
   obtaining a first plurality of images of a subject, the first plurality of images collectively defining a first image volume;
   filtering the first plurality of images to create a second plurality of images, each image in the second plurality of images comprising an average of at least two images in the first plurality of images, wherein each image in the first plurality of images is a thin image, and each image in the second plurality of images is a thick image;
   selecting a first thin image from the first plurality of images;
   adding a lost noise image to a second thick image in the second plurality of images to create a noise restored image, the second thick image in the second plurality of images corresponding to the first thin image in the first plurality of images;
   determining a gradient image based on pixel values in the second plurality of images, the gradient image comprising a gradient value at each pixel location in the second thick image; and
   combining, based on the determined gradient image, the first thin image and the noise restored image to obtain a corrected image in which an appearance of a imaging artifact is reduced; and
   displaying the corrected image.

2. The method of claim 1, wherein the determining step comprises:
   calculating, at each location in the second thick image, directional gradient values that are each based on an absolute value of a change in image intensity at two pixel locations having coordinates that differ only in a respective direction; and
   determining the gradient value at each pixel location in the second thick image as a weighted average of the directional gradient values.

3. The method of claim 2, further comprising low-pass filtering the directional gradient values to obtain filtered directional gradient values, wherein the step of determining the gradient value comprises determining the gradient value at each location in the second thick image as a weighted average of the filtered directional gradient values.

4. The method of claim 1, further comprising:
   obtaining pure noise images corresponding to the first plurality of images;
   filtering the pure noise images to create respective thick noise images, each thick noise image being a weighted average of at least two of the pure noise images; and
   subtracting a thick noise image corresponding to the first thin image from a corresponding pure noise image to create the lost noise image.

5. The method of claim 1, wherein the obtaining step comprises:
   obtaining plural computed tomographic (CT) image slices having a uniform slice spacing as the first plurality of images.

6. The method of claim 1, wherein the filtering step comprises:
   filtering the first plurality of images using one of a weighted average, a non-weighted average, and an adaptively weighted average of at least two of the images in the first plurality of images.

7. The method of claim 6, wherein the filtering step comprises determining the second plurality of images from the equation:

$$THICK[i, j, s] = \sum_{c=-N_{TAvg}/2}^{N_{TAvg}/2} W_{Thk}[c] \cdot ARTIFACT[i, j, s+c],$$

wherein ARTIFACT is the first image volume, THICK is an image volume corresponding to the second plurality of images, $N_{TAvg}$ is a number of images used in averaging, and $W_{Thk}[c]$ are weights.

8. The method of claim 1, further comprising:
   performing image enhancement of each image in the first plurality of images.

9. The method of claim 8, wherein the performing image enhancement step comprises:
   one of (1) image sharpening to enhance image edges of each image in the first plurality of images, and (2) image thickening of each image in the first plurality of images.

10. The method of claim 1, wherein the combining step comprises:
    determining, based on the gradient image, a weight value for each respective pixel location in the first thin image; and
    determining, using the determined weight values, the corrected image as a weighted average of the first thin image and the noise restored image.

11. The method of claim 1, wherein the combining step comprises:
    determining the corrected image using the equation:

$$C[i,j]=W_f\{G[i,j]\} \cdot X[i,j]+(1-W_f\{G[i,j]\}) \cdot Y[i,j],$$

wherein C[i,j] is the corrected image, G[i,j] is the gradient image, X is the first thin image, Y is the noise restored image, and $W_f\{\ \}$ is a weight function that outputs a weight value based on an input gradient value G[i,j].

12. A system for processing a medical image, comprising:
    an apparatus configured to obtain a first plurality of images, the first plurality of images collectively defining a first image volume;

a processor configured to (1) filter the first plurality of images to create a second plurality of images, each image in the second plurality of images comprising an average of at least two images in the first plurality of images, wherein each image in the first plurality of images is a thin image, and each image in the second plurality of images is a thick image; (2) select a first thin image from the first plurality of images; (3) add a lost noise image to a second thick image in the second plurality of images to create a noise restored image, the second thick image in the second plurality of images corresponding to the first thin image in the first plurality of images; (4) determine a gradient image based on pixel values in the second plurality of images, the gradient image comprising a gradient value at each pixel location in the second thick image; and (5) combine, based on the determined gradient image, the first thin image and the noise restored image to obtain a corrected image in which an appearance of an imaging artifact is reduced.

13. A system for processing a medical image, comprising:

a memory configured to store a first plurality of images, the first plurality of images collectively defining an image volume;

a filtering mechanism configured to filter the first plurality of images to create a second plurality of images, each image in the second plurality of images comprising an average of at least two images in the first plurality of images, wherein each image in the first plurality of images is a thin image, and each image in the second plurality of images is a thick image;

a selecting mechanism configured to select a first thin image from the first plurality of images;

an adding mechanism configured to add a lost noise image to a second thick image in the second plurality of images to create a noise restored image, the second thick image in the second plurality of images corresponding to the first thin image in the first plurality of images;

a determining mechanism configured to determine a gradient image based on pixel values in the second plurality of images, the gradient image comprising a gradient value at each pixel location in the second thick image; and a combining mechanism configured to combine, based on the determined gradient image, the first thin image and the noise restored image to obtain a corrected image in which an appearance of an imaging artifact is reduced.

14. The system of claim 13, further comprising:

an image enhancement mechanism configured to perform image enhancement of each image in the first plurality of images.

15. The system of claim 14, wherein the image enhancement mechanism comprises:

one of (1) an image sharpening mechanism configured to enhance image edges of each image in the first plurality of image, and (2) an image thickening mechanism configured to perform image thickening of each image in the first plurality of images.

16. The system of claim 13, further comprising:

a noise obtaining mechanism configured to obtain pure noise images corresponding to the first plurality of images;

a noise filter mechanism configured to filter the pure noise images to create respective thick noise images, each thick noise image being a weighted average of at least two of the pure noise images; and a subtracting mechanism configured to subtract a thick noise image corresponding to the first thin image from a corresponding pure noise image to create the lost noise image.

17. The system of claim 13, further comprising:

a CT obtaining mechanism configured to obtain plural computed tomographic (CT) image slices having a uniform slice spacing as the first plurality of images.

18. The system of claim 13, wherein the filtering mechanism comprises:

an averaging mechanism configured to filter the first plurality of images using one of a weighted average, a non-weighted average, and an adaptively weighted average of at least two of the images in the first plurality of images.

19. The system of claim 18, wherein the filtering mechanism is configured to determine the second plurality of images from the equation:

$$THICK[i, j, s] = \sum_{c=-N_{TAvg}/2}^{N_{TAvg}/2} W_{Thk}[c] \cdot ARTIFACT[i, j, s+c],$$

wherein ARTIFACT is the first image volume, THICK is an image volume corresponding to the second plurality of images, $N_{TAvg}$ is a number of images used in averaging, and $W_{Thk}[c]$ are weights.

20. The system of claim 13, wherein the determining mechanism comprises:

a calculating mechanism configured to calculate, at each location in the second thick image, directional gradient values that are each based on an absolute value of a change in image intensity at two pixel locations having coordinates that differ only in a respective direction; and a weighting mechanism configured to determine the gradient value at each pixel location in the second thick image as a weighted average of the directional gradient values.

21. The system of claim 20, further comprising a low-pass filtering mechanism configured to low-pass filter the directional gradient values to obtain filtered directional gradient values, wherein the weighting mechanism is configured to determine the gradient value at each location in the second thick image as a weighted average of the filtered directional gradient values.

22. The system of claim 13, wherein the combining mechanism comprises:

a determining mechanism configured to determine, based on the gradient image, a weight value for each respective pixel location in the first thin image; and a blending mechanism configured to blend, using the determined weight values, the corrected image as a weighted average of the first thin image and the noise restored image.

23. The system of claim 13, wherein the combining mechanism is configured to determine the corrected image using the equation:

$$C[i,j] = W_f\{G[i,j]\} \cdot X[i,j] + (1 - W_f\{G[i,j]\}) \cdot Y[i,j],$$

wherein C[i,j] is the corrected image, G[i,j] is the gradient image, X is the first thin image, Y is the noise restored image, and $W_f\{\ \}$ is a weight function that outputs a weight value based on an input gradient value $G[i,j]$.

24. A computer readable medium storing program instructions for execution on a computer system, which when executed by the computer system, cause the computer system to process a medical image by performing the steps of:

obtaining a first plurality of images, the first plurality of images collectively defining a first image volume;

filtering the first plurality of images to create a second plurality of images, each image in the second plurality of images comprising an average of at least two images in the first plurality of images, wherein each image in the first plurality of images is a thin image, and each image in the second plurality of images is a thick image;

selecting a first thin image from the first plurality of images;

adding a lost noise image to a second thick image in the second plurality of images to create a noise restored image, the second thick image in the second plurality of images corresponding to the first thin image in the first plurality of images;

determining a gradient image based on pixel values in the second plurality of images, the gradient image comprising a gradient value at each pixel location in the second thick image; and combining, based on the determined gradient image, the first thin image and the noise restored image to obtain a corrected image in which an appearance of an imaging artifact is reduced.

25. The computer readable medium of claim 24, storing further program instructions for execution on the computer system, which when executed by the computer system, cause the computer system to perform the additional steps of:

performing image enhancement of each image in the first plurality of images.

26. The computer readable medium of claim 25, wherein the image enhancement performing step comprises:

one of (1) image sharpening to enhance image edges of each image in the first plurality of images, and (2) image thickening of each image in the first plurality of images.

27. The computer readable medium of claim 24, storing further program instructions for execution on the computer system, which when executed by the computer system, cause the computer system to perform the additional steps of:

obtaining pure noise images corresponding to the first plurality of images;

filtering the pure noise images to create respective thick noise images, each thick noise image being a weighted average of at least two of the pure noise images; and subtracting a thick noise image corresponding to the first image from a corresponding pure noise image to create the lost noise image.

28. The computer readable medium of claim 24, wherein the obtaining step comprises:

obtaining plural computed tomographic (CT) image slices having a uniform slice spacing as the first plurality of images.

29. The computer readable medium of claim 24, wherein the filtering step comprises:

filtering the first plurality of images using one of a weighted average, a non-weighted average, and an adaptively weighted average of at least two of the images in the first plurality of images.

30. The computer readable medium of claim 29, wherein the filtering step comprises determining the second plurality of images from the equation:

$$THICK[i, j, s] = \sum_{c=-N_{TAvg}/2}^{N_{TAvg}/2} W_{Thk}[c] \cdot ARTIFACT[i, j, s+c],$$

wherein ARTIFACT is the first image volume, THICK is an image volume corresponding to the second plurality of images, $N_{TAvg}$ is a number of images used in averaging, and $W_{Thk}[c]$ are weights.

31. The computer readable medium of claim 24, wherein the determining step comprises:

calculating, at each location in the second thick image, directional gradient values that are each based on an absolute value of a change in image intensity at two pixel locations having coordinates that differ only in a respective direction; and determining the gradient value at each pixel location in the second thick image as a weighted average of the directional gradient values.

32. The computer readable medium of claim 31, storing further program instructions for execution on the computer system, which when executed by the computer system, cause the computer system to perform the additional step of low-pass filtering the directional gradient values to obtain filtered directional gradient values, wherein the step of determining the gradient value comprises determining the gradient value at each location in the second thick image as a weighted average of the filtered directional gradient values.

33. The computer readable medium of claim 24, wherein the combining step comprises:

determining, based on the gradient image, a weight value for each respective pixel location in the first thin image; and determining, using the determined weight values, the respective corrected image as a weighted average of the first thin image and the noise restored image.

34. The computer readable medium of claim 24, wherein the combining step comprises:

determining the corrected image using the equation:

$$C[i,j]=W_f\{G[i,j]\}\cdot X[i,j]+(1-W_f\{G[i,j]\})\cdot Y[i,j],$$

wherein $C[i,j]$ is the corrected image, $G[i,j]$ is the gradient image, X is the first thin image, Y is the noise restored image, and $W_f\{\ \}$ is a weight function that outputs a weight value based on an input gradient value $G[i,j]$.

* * * * *